United States Patent [19]

Adelstein et al.

[11] 4,086,227
[45] Apr. 25, 1978

[54] NOVEL ANTI-DIARRHEAL 4-AZATRICYCLO[4.3.1.1^{3,8}] UNDECANE DERIVATIVES

[75] Inventors: Gilbert W. Adelstein, Evanston; Esam Z. Dajani, Buffalo Grove; Chung Hwai Yen, Skokie, all of Ill.

[73] Assignee: G. D. Searle & Co., Chicago, Ill.

[21] Appl. No.: 821,067

[22] Filed: Aug. 2, 1977

Related U.S. Application Data

[62] Division of Ser. No. 733,503, Oct. 18, 1976, Pat. No. 4,057,549, which is a division of Ser. No. 568,439, Apr. 16, 1975, Pat. No. 3,998,832.

[51] Int. Cl.² .................. C07D 223/00; C07D 403/02
[52] U.S. Cl. .......................... 260/239 B; 260/296 D
[58] Field of Search ....................... 260/239 B, 296 D

[56] References Cited

U.S. PATENT DOCUMENTS 3,917,615  11/1975  Adelstein ..................... 260/293.54
3,998,832  12/1976  Adelstein et al. .............. 260/293.54

Primary Examiner—John D. Randolph
Attorney, Agent, or Firm—John J. McDonnell

[57] ABSTRACT

The present invention, comprehends a method for treating diarrhea comprising administering to an animal in need of anti-diarrheal treatment an effective anti-diarrheal amount of a compound of the formula

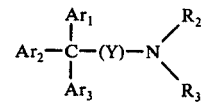

and acid addition salts thereof wherein Y is alkylene containing 1–4 carbon atoms; $R_2$ and $R_3$ together with N is a heterocyclic ring system comprising azamonocyclic ring of the formula

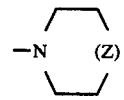

wherein Z is phenylhydroxymethylmethylene, phenylhydroxymethylene, phenylcarboxymethylene, phenylcarbalkoxymethylene or azabicycloalkyl or phenyl or hydroxyl substituted azabicycloalkyl containing 6–9 carbon atoms and containing at least 5 atoms in each ring of the azabicycloalkyl or 4-azatricyclo[4.3.1.1^{3,8}]undec-4-yl; $Ar_1$ and $Ar_2$ are phenyl, halo-substituted phenyl, (lower alkyl) substituted phenyl, pyridyl, thienyl or furyl, and $Ar_3$ is phenyl, halo-substituted phenyl, (lower alkyl) substituted phenyl, pyridyl, thienyl, furyl, pyrrolyl, imidazoyl, oxazolinyl, oxazolyl, thiazolinyl, thiazolyl, 1,2,4-oxodiazolyl, and isoxazolinyl. The present invention also comprehends novel compounds included in the above formula.

1 Claim, No Drawings

NOVEL ANTI-DIARRHEAL 4-AZATRICYCLO[4.3.1.1$^{3,8}$] UNDECANE DERIVATIVES

This is a division of Ser. No. 733,503 filed Oct. 18, 1976, now U.S. Pat. No. 4,057,549, which is in turn a division of Ser. No. 568,439, filed Apr. 16, 1975, now U.S. Pat. No. 3,998,832.

The present invention encompasses a method for treating diarrhea comprising administering to an animal in need of antidiarrheal treatment an effective antidiarrheal amount (0.1 to 25 mpk) of a compound of the formula

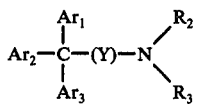

and the pharmaceutically acceptable acid addition salts thereof wherein Y is alkylene containing 1–4 carbon atoms; $R_2$ and $R_3$ together with N is a heterocyclic ring system comprising azamonocyclic ring of the formula

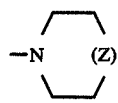

wherein Z is hydroxymethylmethylene, phenylhydroxymethylmethylene, phenylhydroxymethylene, phenylcarboxymethylene, phenylcarbalkoxymethylene or an azabicycloalkyl or phenyl or hydroxyl substituted azabicycloalkyl containing 6–9 carbon atoms and containing at least 5 atoms in each ring of the azabicycloalkyl or 4-azatricyclo[4.3.1.1$^{3,8}$]undec-4-yl; $Ar_1$ and $Ar_2$ are phenyl, halo-substituted phenyl, (lower alkyl) substituted phenyl, pyridyl, thienyl or furyl, and $Ar_3$ is phenyl, halo-substituted phenyl, (lower alkyl) substituted phenyl, pyridyl, thienyl, furyl, pyrrolyl, imidazoyl, oxozolyl, oxazolinyl, thiazolinyl, thiazolyl, 1,2,4-oxodiazolyl, and isoxazolinyl.

Embodiments of the present invention involving administration of compounds of the formula

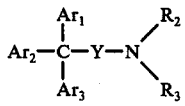

or acid addition salts thereof wherein $R_2$ and $R_3$ together with N is an azabicycloalkyl containing 6–9 carbon atoms and containing at least 5 atoms in each ring of the azabicycloalkane; $Ar_1$ and $Ar_2$ are phenyl, halo-substituted phenyl, (lower alkyl) substituted phenyl, pyridyl, thienyl, or furyl, and $Ar_3$ is phenyl, halo-substituted phenyl, (lower alkyl) substituted phenyl, pyridyl, thienyl, furyl, Y is alkylene containing 1–4 carbon atoms are illustrated by the administration to an animal in need of anti-diarrheal treatment an effective antidiarrheal amount of 2-(3,3,3-triphenylpropyl)-2-azabicyclo[2.2.2]-octane, 2-3,3-diphenyl-3-(2-pyridyl)propyl]-2-azabicyclo[2.2.2]octane, 2-[3,3diphenyl-3-(3-pyridyl)propyl]-2-azabicyclo[2.2.2]-octane, 2-[3,3,diphenyl-3-(2-furyl)-propyl]-2-azabicyclo-[2.2.2]octane, or 2-[3,3-diphenyl-3-(2-thienyl)propyl]-2-azabicyclo[2.2.2]octane.

An embodiment of the present invention comprises a method of treating diarrhea comprising administering to an animal in need of anti-diarrheal treatment an effective antidiarrheal amount (0.1 to 25 mpk) of a compound of the formula

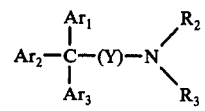

and pharmaceutically acceptable acid addition salts thereof wherein Y is alkylene containing 1–4 carbon atoms; $R_2$ and $R_3$ together with N is heterocyclic ring system comprising azamonocyclic ring of the formula

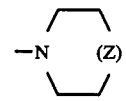

wherein Z is hydroxymethylmethylene phenylhydroxymethylene, phenylcarboxymethylene, phenylcarbalkoxymethylene or an azabicycloalkyl or phenyl or hydroxyl substituted azabicycloalkyl containing 6 to 9 carbon atoms and containing at least 5 atoms in each ring of the azabicycloalkyl or 4-azatricyclo[4.3.1.1$^{3,8}$]undec-4-yl; $Ar_1$, $Ar_2$ and $Ar_3$ are phenyl, halo-substituted phenyl, (lower alkyl) substituted phenyl, pyridyl, thienyl or furyl.

The present invention encompasses a compound of the formula

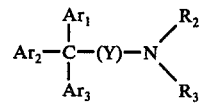

and the pharmaceutically acceptable acid addition salts thereof wherein Y is alkylene containing 1–4 carbon atoms; $R_2$ and $R_3$ together with N is a heterocyclic ring system comprising azamonocyclic ring of the formula

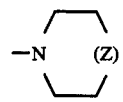

wherein Z is hydroxymethylmethylene, phenylhydroxymethylmethylene, phenylhydroxymethylene, phenylcarboxymethylene, phenylcarbalkoxymethylene or azabicycloalkyl or phenyl or hydroxyl substituted azabicycloalkyl containing 6 to 9 carbon atoms and containing at least 5 atoms in each ring of the azabicycloalkyl or 4-azatricyclo[4.3.1.1$^{3,8}$]undec-4-yl; $Ar_1$ and $Ar_2$ are phenyl, halo-substituted phenyl, (lower alkyl) substituted phenyl, pyridyl, thienyl or furyl, and $Ar_3$ is phenyl, halo-substituted phenyl, (lower alkyl) substituted phenyl, pyridyl, thienyl, furyl, pyrrolyl, imidazoyl, oxazolyl, oxazolinyl, thiazolinyl, thiazolyl, 1,2,4-oxodiazolyl, and isoxazolinyl. The term halo includes fluor, chloro, bromo, and iodo. The term lower alkyl includes alkyl radicals having 1–7 carbon atoms such as methyl, ethyl, propyl, isopropyl, butyl, pentyl, hexyl, and heptyl. The term alkylene containing 1–4 carbon atoms includes such alkylene radicals as methylene, ethylene, propylene, isopropylene, and butylene.

Compounds in which $R_2$ and $R_3$ together with N is an azabicycloalkane or phenyl or hydroxyl substituted azabicycloalkane containing 6-9 carbon atoms and containing at least 5 atoms in each ring and wherein $Ar_1$, $Ar_2$, and $Ar_3$ as defined in the preceeding paragraph are particularly useful in practicing the present invention in that they are potent antidiarrheal agent with minor, if any, central nervous system effect i.e., there is unexpectedly a distinct separation of central nervous system and antidiarrheal properties. These compounds are antidiarrheal compounds without central nervous system effecting properties. Compounds of the formula

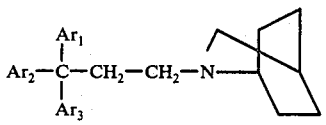

and acid addition salts thereof wherein $Ar_1$ and $Ar_2$ are phenyl, halo-substituted phenyl, (lower alkyl) substituted phenyl, pyridyl, thienyl, or furyl, and $Ar_3$ is phenyl, halo-substituted phenyl, (lower alkyl) substituted phenyl, pyridyl, thienyl, furyl, pyrrolyl, imidazoyl, oxazolinyl isoxazolinyl, thiazolinyl, thiazolyl, 1,2,4-oxadiazolyl or isoxazolinyl are particularly preferred. Other preferred azabicyclo radicals such as 3-azabicyclo[3.2.2]non-3-yl, 6-azabicyclo[3.2.1]oct-6-yl, 7-azabicyclo[2.2.1]hept-7-yl, 8-azabicyclo[4.3.0]non-8-yl, 2-azabicyclo[3.3.1]non-2-yl, 5-hydroxy-2-azabicyclo[2.2.2]oct-2-yl, 5-hyroxy-5-phenyl-2-azabicyclo[2.2.2]oct-2-yl, 4-phenyl-2-azabicyclo[2.2.2]-oct-2-yl, 2-aza-5,6,1; 2-(benzo)bicyclo[2.2.2]oct-2-yl, 6-hydroxy-2-azabicyclo-[2.2.2]oct-2-yl, and 2-aza-4-phenyl-5,6,1′,2′(benzo)bicyclo[2.2.2]oct-2-yl and 2-azabicyclo[2.2.1]hept-2-yl may replace the 2-azabicyclo[2.2.2]-oct-2-yl radical.

Compounds of the formula

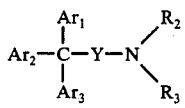

and the pharmaceutically acceptable acid addition salts thereof wherein $R_2$ and $R_3$ together with N is an azabicycloalkyl or phenyl or hydroxyl substituted azabicycloalkyl having 6-9 carbon atoms and having at least 5 atoms in each ring; $Ar_1$ and $Ar_2$ are phenyl, halo-substituted phenyl, (lower alkyl) substituted phenyl, pyridyl, thienyl or furyl; and $Ar_3$ is phenyl, halo-substituted phenyl, (lower alkyl) substituted phenyl, pyridyl, thienyl, furyl are preferred.

Compounds of the formula

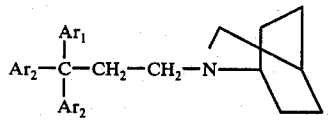

and the pharmaceutically acceptable acid addition salts thereof wherein $Ar_1$ and $Ar_2$ are phenyl, halo-substituted phenyl, (lower alkyl) substituted phenyl, pyridyl, thienyl or furyl, and $Ar_3$ is phenyl, halo-substituted phenyl, (lower alkyl) substituted phenyl pyridyl, thienyl, or furyl are further preferred.

Compounds of the formula

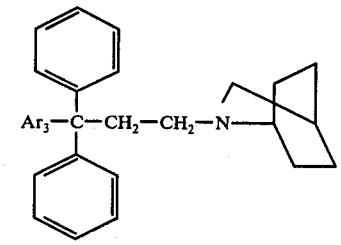

and the acid addition salts thereof wherein $Ar_3$ is phenyl, halo-substituted phenyl, (lower alkyl) substituted phenyl, pyridyl, thienyl, furyl, pyrrolyl, imidazoyl, oxazolyl, oxazolinyl, thiazolinyl, thiazolyl, 1,2,4-oxadiazolyl, or isoxazolinyl are preferred.

Compounds of the above formula wherein $Ar_3$ is phenyl or pyridyl are especially preferred by virtue of separation of anti-diarrheal and central nervous system affecting properties.

Compounds of the formula

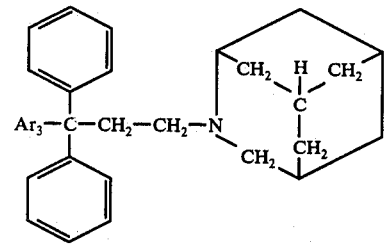

and the pharmaceutically acceptable acid addition salts wherein $Ar_3$ is phenyl or pyridyl are likewise useful anti-diarrheal agents. These compounds are exemplified by 4-[3,3-(diphenyl)-3-(-3-pyridyl)propyl]-4-azatricyclo[4.3.1.1$^{3,8}$]undecane and 4-(3,3,3-triphenylpropyl)-4-azatricyclo[4.3.1.1$^{3,8}$]undecane.

Compounds of the formula

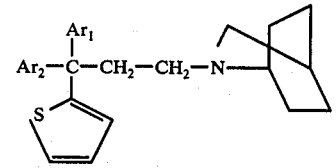

and the pharmaceutically acceptable acid addition salts thereof wherein $Ar_1$ and $Ar_2$ are phenyl, halosubstituted phenyl, (lower alkyl) substituted phenyl, or pyridyl are also preferred. For example 2-[3,3-diphenyl-3-(2-thienyl)propyl]-2-azabicyclo[2.2.2]octane is preferred.

Compounds of the formula

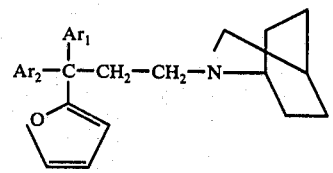

and the acid addition salts thereof wherein $Ar_1$ and $Ar_2$ are defined as before are preferred. For example 2-[3,3-diphenyl-3-(2-furyl)propyl]-2-azabicyclo[2.2.2]=octane is preferred.

Compounds of the formula

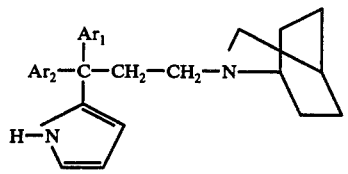

and the acid addition salts thereof wherein $Ar_1$ and $Ar_2$ are as defined earlier are also preferred.

Compounds of the formula

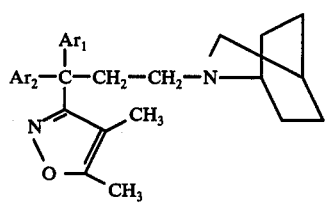

and the acid addition salts thereof wherein $Ar_1$ and $Ar_2$ are as defined earlier are also preferred.

Compounds of the formula

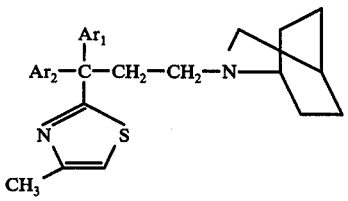

and the acid addition salts thereof wherein $Ar_1$ and $Ar_2$ are as defined earlier are also preferred.

Compounds of the formula

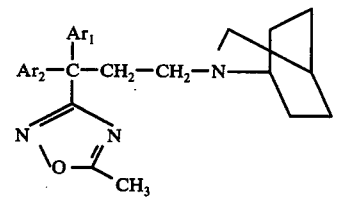

and the acid addition salts thereof wherein $Ar_1$ and $Ar_2$ are as defined earlier are also preferred.

Compounds of the formula

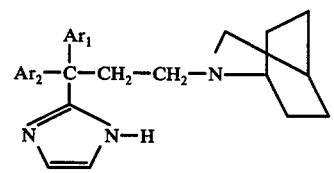

and the acid addition salts thereof wherein $Ar_1$ and $Ar_2$ are as defined earlier are also preferred.

Compounds of the present invention are prepared by the method set out in Scheme I

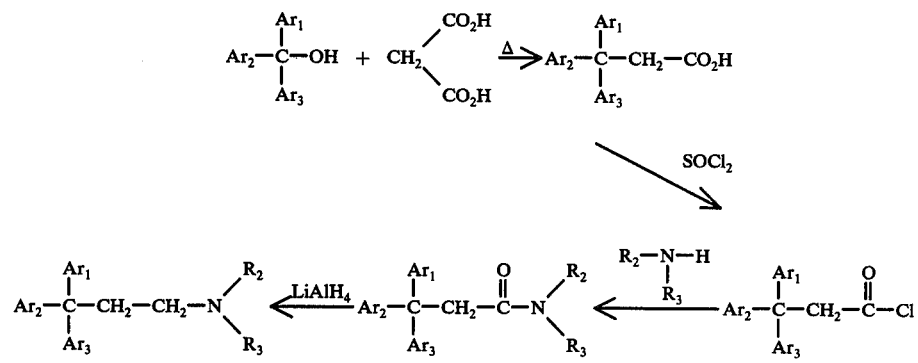

wherein $Ar_1$, $Ar_2$, $Ar_3$, $R_1$ and $R_2$ are as previously described.

SCHEME I

Esters described in U.S. Pat. No. 3,839,576 are suitable intermediates for compounds useful in practicing the present invention. Thus compounds of the formula

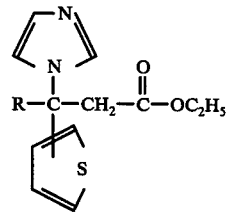

wherein R is phenyl or thienyl may be hydrolysed to the corresponding acid by alcoholic potassium hydroxide and the resulting acid may be converted to the corresponding acid chloride which, in turn, is converted to the compounds of the present invention as set out in Scheme I.

Scheme I represents a combination of methods described by S. Patai and S. Dayagi J. C. S. 716 (1962) and D. Martensson and E. Nilsson Acta Chem. Scand. 19 (3) 711 (1965), CA-63-6968h.

Alternately compounds prepared in Scheme I may be produced by the following reaction

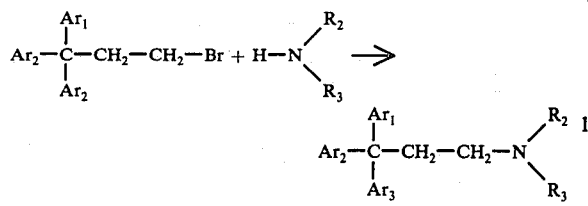

The organic bases of this invention form non-toxic, acid-addition salts with a variety of organic and inorganic acids. Such salts are formed with acids such as sulfuric, phosphoric, hydrochloric, hydrobromic, hydriodic, sulfamic, citric, lactic, maleic, malic, succinic, tartaric, cinnamic, acetic, benzoic, gluconic, ascorbic and related acids.

The starting alcohol shown in Scheme I is prepared as shown in Scheme II.

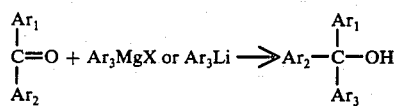

SCHEME II

Thus 1 part of triphenylcarbinol is reacted with 2 parts of malonic acid at 170° for 3 hours to provide 3,3,3-triphenylpropionic acid and this acid is converted into the acid chloride by reaction with thionyl chloride. Reacting the acid chloride with 2 parts of 2-azabicyclo[2.2.2]octane provides the amide, 2-(3,3,3-triphenylpropionyl)-2-azabicyclo[2.2.2]octane and reduction of this amide with 1 part of LiAlH₄ in tetrahydrofuran provides 2-(3,3,3-triphenylpropyl)-2-azabicyclo[2.2.2]-octane. The addition of concentrated hydrochloric acid to an ethereal solution of above amine provides 2-(3,3,3-triphenyl propyl)-2-azabicyclo[2.2.2]octane hydrochloride, melting at 221°-223° C.

Alternately compounds of the present invention may be prepared as set out in Scheme III

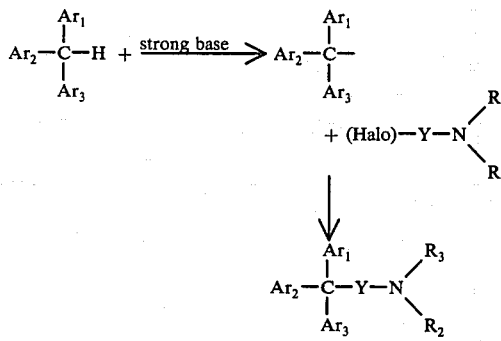

SCHEME III

This method represents a modification of methods described by Martensson and Nilson, Acta Chem. Scand. 19 )3), 711-12 (1965) - CA-63-6968h. Thus, 1 part of 2-(2-phenylbenzyl) pyridine is reacted with 1 part of n-Butyl lithium in tetrahydrofuran at −70° C. and then reacted with 1 part of 2-(2-chloroethyl)-2-azabicyclo[2.2.2]octane to provide 2-[3,3-diphenyl-3-(2-pyridyl)propyl]-2-azabicyclo[2.2.2]octane.

Ring closure methods are also useful for preparing compounds of the present invention as set out in Scheme IV.

IV A.

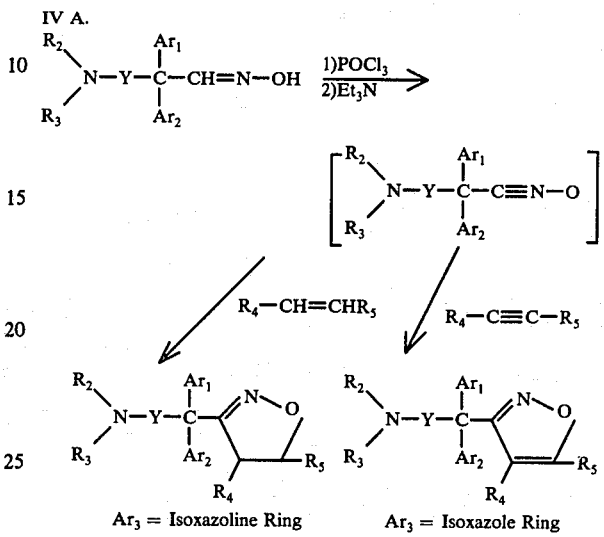

wherein Y, $R_2$, $R_3$, $Ar_1$ and $Ar_2$ are as defined before and $R_4$ and $R_5$ are lower alkyl containing 1-7 carbon atoms or hydrogen.

IV B.

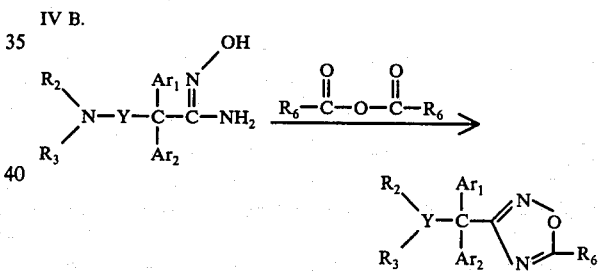

wherein Y, $R_2$, $R_3$, $Ar_1$ and $Ar_2$ are as defined before and $R_6$ is lower alkyl containing 1-7 carbon atoms.

IV C.

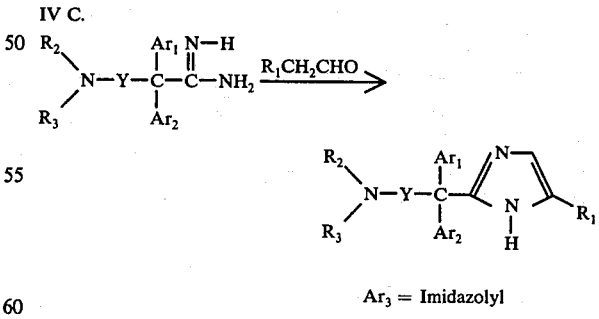

Ar₃ = Imidazolyl wherein Y, $R_2$, $R_3$, $Ar_1$ and $Ar_2$ are as defined before.

IV D.

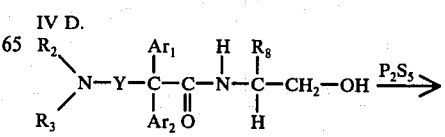

-continued

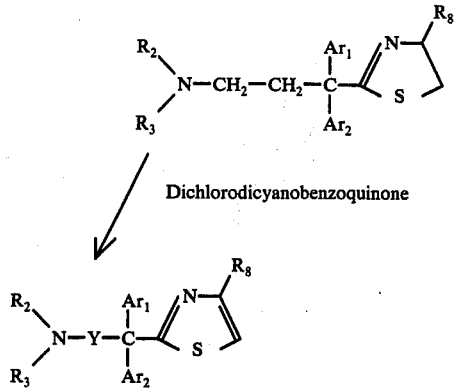

Dichlorodicyanobenzoquinone wherein Y, $R_2$, $R_3$, $Ar_1$ and $Ar_2$ are as previously described and $R_8$ is lower alkyl containing 1–7 carbon atoms.

Anti-diarrheal utility of the instant compounds is evidenced by their ability to inhibit gastrointestinal propulsion as set out in the following test.

CHARCOAL MEAL TEST

Mice weighing 18–24 grams and previously fasted for 24 hours are each given orally 0.2 ml. of a suspension containing 10% charcoal and 1% methylcellulose. The test compounds are administered intragastrically one hour prior to the charcoal meal. 3.5 Hours after administration of the meal the mice are sacrificed by cervicle dislocation and the cecum is examined for the presence of absence of charcoal on an all or none basis. Each compound is tested at three dose levels (typically 30, 10, 3 mg/kg) in groups of 6 mice per dose level. Control groups of mice given saline only were run concurrently with each test group.

CASTOR OIL-INDUCED DIARRHEA TEST

Following the experimental design of Niemegear et al. Arzniem - Forsch 22: 515–518 (1972). Adult male Charles River rats weighing 180–200 grams in groups of 12 are fasted in community cages for 24 hours prior to the test with free access to water. The test compounds were in 0.5% methyl cellulose suspension at 2.0 ml/kg. The control constitutes the vehicle only. One hour after the compound administration, 1.0 m. of castor-oil was given to each rat intragastrically. The rats were then observed for the presence or absence of diarrhea at hourly intervals for up to 8 hours, post administration of castor-oil. The median effective dose value (ED50) was calculated using the method of Berkson, J. Amer. Statist, Assoc. 48 565–99 (1953). Lack of central nervous system effective properties are shown by the following test.

MOUSE HOT PLATE TEST

A mouse (adult male weighing 18–25 grams) is placed in a restraining cylinder on a hot plate with the temperature controlled at 55 ± 0.3° C. The reaction time of the mouse to lick a foot or jump is measured at 60, 40 and 20 minutes before and 30, 60, 90, and 120 minutes after administration of the test compound. The "normal" reaction time is measured as the median of the three pretreatment reaction times. A positive response consists of a reaction time greater than twice the normal time at any of the post treatment times. A dose (50 mg/kg administered intraperitoneally) of the test compound is considered active when 50 percent or more of the animals used show a positive response.

TAIL CLIP TEST

A special clip is applied to the base of the tail of the mouse (adult male weighing 18–25 grams) and the time for the animal to turn around to bit at it is measured. The sensitivity of each mouse is determined one-half hour prior to drug administration. Only those mice attempting to bite the clip are included in the experiment. The test compound is then administered intraperitoneally and the response to placement of the clip is determined at 30, 60, 90, and 120 minutes after treatment. A response is considered positive if the animal takes more than 2 times the pre-drug time to bite at the clip at any of these time intervals. A test compound is considered active when 50 percent or more of the animals used show a positive response.

The compounds herein described can be combined with pharmaceutically acceptable carriers to provide novel pharmaceutical compositons. The concentration of active ingredient in the composition is not critical, but is preferably 1–80%. These compositions ca be administered orally, suitable forms for such administration including tablets, lozenges, capsules, dragees, pills, powders, solutions, suspensions and syrups. Acceptable pharmaceutical carriers are exemplified by gelatin capsules; sugars such as lactose or sucrose; starches such as corn starch or potato starch; cellulose derivatives such as sodium carboxymethyl cellulose, ethyl cellulose, methyl cellulose, or cellulose acetate phthalate; gelatin; talc; calcium phosphates such as dicalcium phosphate or tricalcium phosphate; sodium sulfate; calcium sulfate; polyvinyl pyrrolidone; acacia; polyvinyl alcohol; stearic acid; alkaline earth metal stearates such as magnesium stearate; oils such as peanut oil, cottonseed oil, sesame oil; olive oil, corn oil, oil of theobroma; water; agar; alginic acid; and benzyl alcohol, as well as other non-toxic compatible substances used in pharmaceutical formulations.

The compounds of this invention can be used to produce an antidiarrheal effect in mammals by administering the instant novel compositions containing a therapeutically effective amount of the active ingredient. The term "therapeutically effective amount" is defined as the amount of active ingredient that will produce an antidiarrheal effect, i.e., which will reverse, inhibit or prevent diarrhea. For a particular subject, the amount of active ingredient to be used will vary with the subject involved, the severity of the diarrhea, and the particular active ingredient used. The therapeutically effective amount of a particular active ingredient can be determined by comparing its potency to that of a known standard, for which the therapeutic dosage is known. Typically 0.1–25 mg./kg. is an effective antidiarrheal amount of a given compound.

Those skilled in the art will recognize that observations of activity in standardized tests for particular biological effects are fundamental to the development of valuable new drugs, both veterinary and human.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set

EXAMPLE 1

A mixture of 2 parts of triphenyl carbinol and 8 parts of malonic acid are heated at 170° for 3 hours. This mixture is cooled and dissolved in hot ethanol. 3,3,3-Triphenylpropionic acid, melting at 182°, crystallizes from the ethanol upon cooling. 1 Part of 3,3,3-triphenylpropionic acid is refluxed with 5 parts of thionyl chloride for 4 hours and the excess thionyl chloride is removed in vacuum to provide the crude 3,3,3-triphenyl propionyl chloride. 1 Part of this acid chloride is reacted with 2 parts of 2-azabicyclo[2.2.2]octane in 50 parts of benzene. The precipitated amide is filtered and the benzene solution washed with water, dried with magnesium sulfate, and the benzene evaporated. The remaining oil is crystallized to provide 2-(3,3,3-triphenylpropionyl)-2-azabicyclo[2.2.2]octane. 0.9 Parts of this material is reacted with 0.37 parts of lithium aluminum hydride in 15 parts of tetrahydrofuran at reflux for 5 hours. The reaction mixture is cooled and treated with 15% aqueous sodium hydroxide solution to decompose any unreacted lithium aluminum hydride. The reaction mixture is filtered and the solvent is removed in vacuo to provide a residual oil which is taken up in ether. The ether soln. is extracted c̄ 10% HCl forming an insoluble gum, which is dissolved in methylene chloride, dried over anhydrous sodium sulfate and evaporated providing 2-(3,3,3-triphenylpropyl)-2-azabicyclo[2.2.2]octane hydrochloride, melting at 222°–223° C. This compound has the following molecular formula.

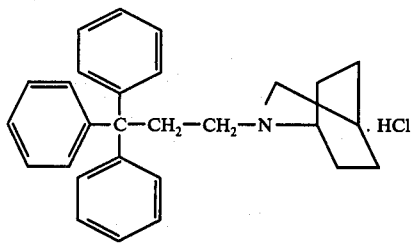

This compound has an ED50 = 6.3 ± 3.0 mkp via intragastric administration to mice in the charcoal meal test.

EXAMPLE 2

Following the procedures set out in Example 1, 1 part of 3,3,3-triphenylpropionyl chloride and 2 parts of 4-hydroxy-4-phenylpiperidine are reacted to provide 1-(3,3,3-triphenylpropionyl)-4-hydroxy-4-phenylpiperidine. 0.23 Parts of this amide is reacted with 0.05 parts of lithium aluminum hydride in 3.0 parts by volume of ethyl ether to provide 1-(3,3,3-triphenylpropyl)-4-hydroxy-4-phenylpiperidine. This compound has the following structural formula

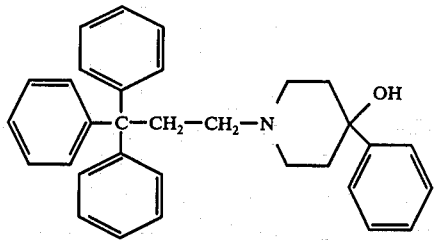

Administration of this material inhibits diarrhea in animals in need of antidiarrheal treatment.

EXAMPLE 3

Following the procedures set out in Example 1, 1 part of 3,3,3-triphenylpropionyl chloride and 2 parts of hexahydroazepine are reacted to provide 1=(3,3,3-thiphenylpropionyl)hexahydroazepine. 0.4 Part of this amide is reacted with 0.05 part of lithium aluminum hydride in 3.0 parts by volume of ethyl ether to provide 1-(3,3,3-triphenylpropyl)hexahydroazepine. This compound has the following structural formula.

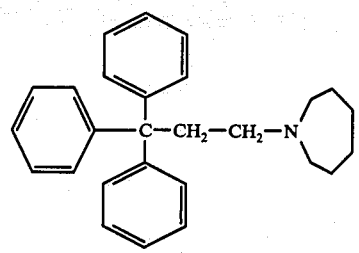

1-(3,3,3-triphenylpropyl)hexahydroazepine hydrochloride melting at 208°–211° is prepared by treating the free base with hydrochloric acid.

EXAMPLE 4

1 Part of 3,3-(diphenyl)-3-(2-thienyl)propionyl chloride (Martenson and Nilson Acta Chem. Scand. 19 711, (1965) is reacted with 20 parts of 2-azabicyclo[2.2.2]octane in 50 parts of benzene. The precipitated amide is filtered and the benzene solution washed with water, dried with magnesium sulfate, and the benzene evaporated. The remaining oil is crystallized to provide 2-[3,3-diphenyl-3-(2-thienyl)propionyl]2-azabicyclo[2.2.2]octane. This amide is reduced with lithium aluminum hydride as described in Example 1 to provide 2-[3,3-diphenyl-3-(2-thienyl)propyl]2-azabicyclo[2.2.2]-octane. This compound has the following structural formula

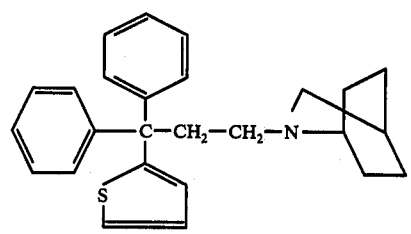

EXAMPLE 5

Reaction of 2.5 parts of diphenyl-2-pyridylmethane in 60 parts by volume of cyclohexane with an equivalent of butyl lithium at 10° C. under nitrogen is followed by the addition of 2.1 parts 2-(2-chloroethyl)-2-azabicyclo[2.2.2]octane in cyclohexane provide after quenching and isolation 2-[3,3-diphenyl-3-(2-pyridyl)propyl]-2-azabicyclo[2.2.2]octane as an oil. Reaction of this amine with oxalic acid in methanol provides the oxalic acid salt, melting at 191.5°–192.5°, having the following formula.

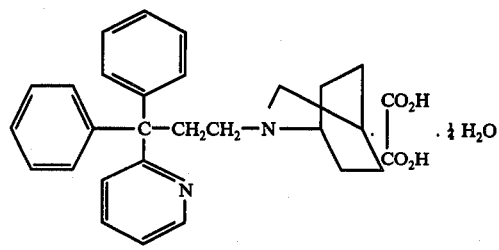

EXAMPLE 6

Following the procedure in Example 5 and substituting 0.39 parts of soda amide for butyl lithium and 2.5 parts of diphenyl-4-pyridylmethane for the 2-pyridyl isomer provides 2-[3,3-diphenyl-3-(4-pyridyl)propyl]-2-azabicyclo[2.2.2]octane, melting at 112°–114° C. This compound has the following formula.

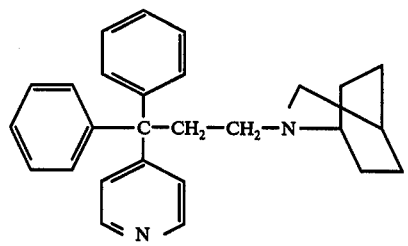

EXAMPLE 7

Following the procedure in Example 1, 2 parts of di-4-methoxyphenyl-4-methylphenylcarbinol is converted to 2-[3,3-(4-methoxyphenyl)-3-(4-methylphenyl)propyl]-2-azabicyclo[2.2.2]octane. This compound has the following structural formula.

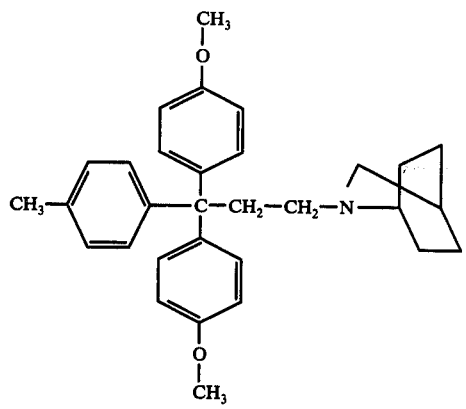

EXAMPLE 8

Following the procedure in Example 1, 2 parts of di-4-chlorophenyl-4-ethoxyphenylcarbinol is converted to 2-[3,3-(4-chlorophenyl)-3-(4-ethoxyphenyl)propyl]-2-azabicicyclo[2.2.2]octane. This compound has the following structural formula.

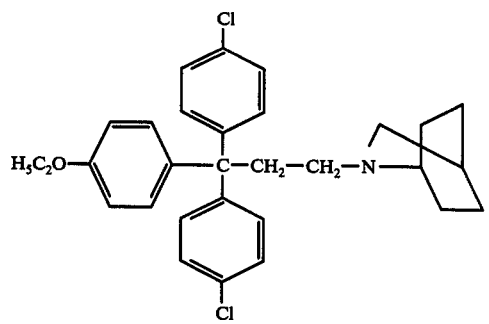

EXAMPLE 9

Following the procedure in Example 1, 2 parts of diphenyl-2-(4-methyl-2-furyl)carbinol is converted to 2-[3,3-diphenyl,-3(5-methyl-2-furyl)propyl]-2-azabicyclo[2.2.2]octane. This compound has the following structural formula.

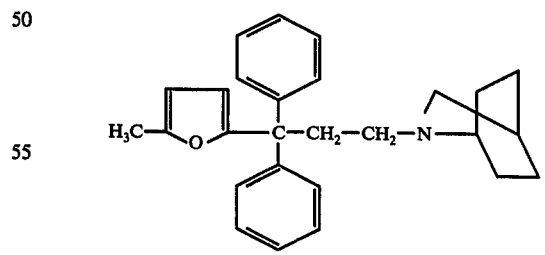

EXAMPLE 10

Following the procedure in Example 1, 2 parts of di-(4-fluorophenyl)-4-ethylcarbinol and using 6-azabicyclo[3.2.1]octane as the amine is converted to 6-[3,3-(4-fluorophenyl)-3-(4-ethylphenyl)propyl]-6-azabicyclo[3.2.1]octane having the following structural formula.

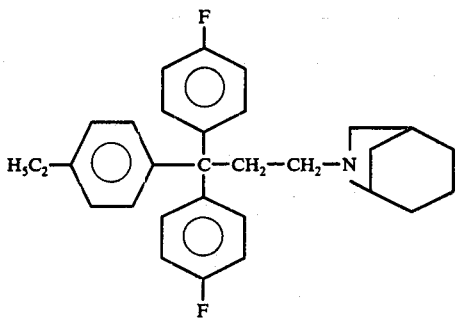

EXAMPLE 11

Following the procedures set out in Example 1, 27.0 parts of norpethidine is reacted with 9 parts of triphenylpropionic acid chloride in the presence of 4 parts of triethylamine in benzene solvent. The resulting amide is reduced with 5 parts of lithium aluminum hydride to provide 1-(3,3,3-triphenylpropyl)-4-hydroxymethyl-4-phenylpiperidine.

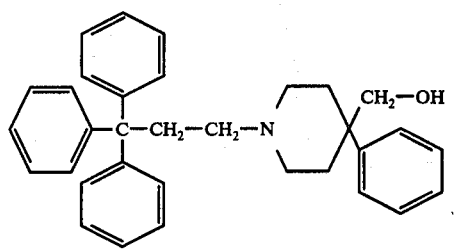

Administration of this material inhibits diarrhea in animals in need of antidiarrheal treatment.

EXAMPLE 12

Following the procedures set out in Example 1, 1 part of 3,3,3-triphenylpropionyl chloride and 2 parts of 5-hydroxy-2-azabicyclo[2.2.2]octane are reacted to provide 2-(3,3,3-triphenylpropionyl)-5-hydroxy-2-azabicyclo[2.2.2]octane. 0.23 Parts of this material is reacted with 0.05 parts of lithium aluminum hydride in 3.0 parts by volume of ethyl ether to provide 2-(3,3,3-triphenylpropyl)-5-hydroxy-2-azabicyclo[2.2.2]octane. This compound, isolated as the hydrochloride salt, has the following structural formula.

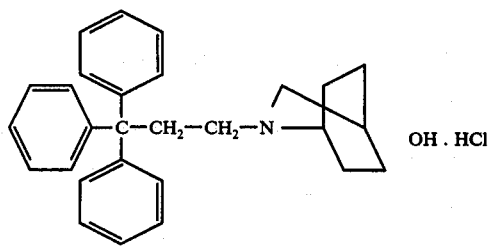

Administration of this material inhibits diarrhea in animals in need of antidiarrheal treatment.

EXAMPLE 13

Following the procedures set out in Example 1, 1 part of 3,3,3-triphenylpropionyl chloride and 2 parts of 2-azabicyclo[3.3.1]nonane are reacted to provide 2-(3,3,3-triphenylpropionyl)-2-azabicyclo[3.3.1]nonane. 0.23 Parts of this amide is reacted with 0.05 parts of lithium aluminum hydride in 3.0 parts by volume of ethyl ether to provide 2-(3,3,3-triphenylpropyl)-2-azabicyclo[3.3.1]nonane. This compound, isolated as the hydrochloride, has the following structural formula.

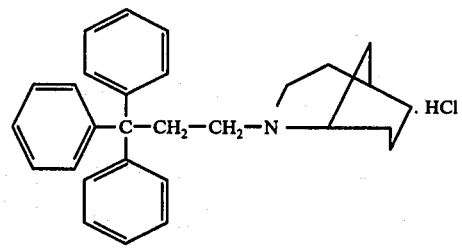

Administration of this material inhibits diarrhea in animals in need of antidiarrheal treatment.

EXAMPLE 14

Following the procedures set out in Example 1, 1 part of 3,3,3-triphenylpropionyl chloride and 2 parts of 4-phenyl-2-azabicyclo[2.2.2]octane are reacted to provide 2-(3,3,3-triphenylpropionyl)-4-phenyl-2-azabicyclo[2.2.2]octane. 0.23 Parts of this material is reacted with 0.05 parts of lithium aluminum hydride in 3.0 parts by volume of ethyl ether to provide 2-(3,3,3-triphenylpropyl)-4-phenyl-2-azabicyclo[2.2.2]octane. This compound isolated as the hydrochloride, has the following structural formula.

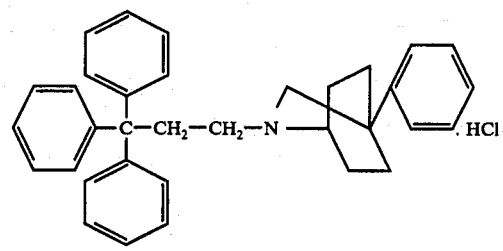

Administration of this material inhibits diarrhea in animals in need of antidiarrheal treatment.

EXAMPLE 15

Following the procedures set out in Example 1, 3.0 parts of 3,3,3-triphenylpropionyl chloride and 2.0 parts of acenaphto[1,2-C]pyrrolidene are reacted to provide 8-(3,3,3-triphenylpropionyl)acenaphto[1,2-C]pyrrolidine, melting at 159°-168°. 3.5 Parts of this amide are reacted with 3.6 parts of lithium aluminum hydride in tetrahydrofuran to provide 8-(3,3,3-triphenylpropyl-)acenaphtho[1,2-C]pyrrolidine. This compound has the following structural formula.

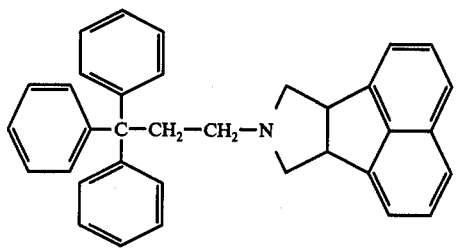

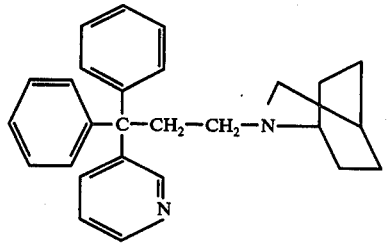

EXAMPLE 16

Following the procedures set out in Example 1, 3.0 parts of 3,3,3-triphenylpropionyl chloride and 2.0 parts of benzo[C]tetrahydropyridine are reacted to provide 2-(3,3,3-triphenylpropinyl)benzo[C]tetrahydropyridine hydrochloride. 4.6 Parts of this amide and 3.0 parts of lithium aluminum hydride in tetrahydrofuran to provide 2-(3,3,3-triphenylpropyl)benzo[C]tetrahydropyridine hydrochloride, melting at 216°–223°. This compound has the following structural formula.

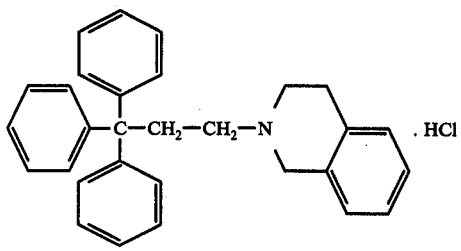

EXAMPLE 17

Following the procedure set out in Example 1, 3.0 parts of 3,3,3-triphenylpropionyl chloride and 2.0 parts of ethyl isonipecotate are reacted to provide 2-(3,3,3-triphenylpropionyl)-4-ethoxycarbonyl piperidine. Reduction of 5.0 parts of this material with 3.0 parts of lithium aluminum hydride in tetrahydrofuran provides 1-(3,3,3-triphenylpropyl)-4-hydroxymethylpiperidine, melting at 142.5°–144°. This compound has the following structural formula.

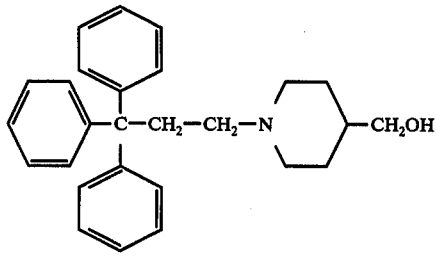

EXAMPLE 18

Following the procedure set out in Example 5, and substituting 0.39 parts of soda amide for butyl lithium and 2.5 parts of diphenyl-3-pyridyl methane for the 2-pyridyl isomer provides 2-[3,3-diphenyl-3-(3-pyridyl)-propyl]azabicyclo[222]octane. This compound has the following structural formula.

EXAMPLE 19

To 3.5 parts of 4-(2-azabicyclo-2.2.2-octane-2-yl(2,2-diphenylbutyraldehyde oxime — prepared from the corresponding nitrile by reduction with diisobutyl aluminim hydride, followed by hydrolysis, and reaction with hydroxyl amine to provide the oxime — in 100 parts of dry benzene is added 2 parts of phosphoryl chloride and the mixture is refluxed for 30 minutes. The solvent is removed under pressure and the resiude taken up in 50 parts of dry toluene, cooled to 0° C, and a cold solution of 1 part of triethylamine and 5 parts of 2-butyne in 10 parts of toluene. The mixture is stirred at 0° for 3 hours, washed with water, and the solvents evaportated. The residue is crystallized from ether-hexane to provide 3-[1,1-dipehnyl-3-(2-azabicyclo[2.2.2]oct-2-yl)propyl]4,5-dimethylisoxazole. This compound has the following structural formula.

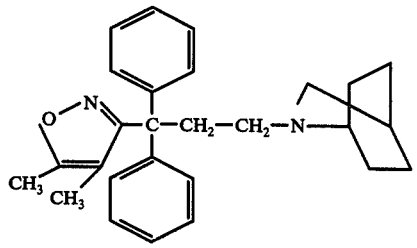

EXAMPLE 20

To 3.6 parts of 4-(2-azabicyclo-2.2.2-oct-2-yl)-2,2-diphenylbutyramidoxime (prepared by the reaction of the corresponding nitrile with hydroxylamine in methanol/ sodium methoxide) in 20 parts of dry pyridine is added 5 parts of acetic anhydride. The mixture is heated by steam for 1 hour and the solvent is evaporated at reduced pressure. The residue is stirred in dilute sodium bicarbonate solution and extracted into methylene chloride. The methylene chloride is separated and removed by evaporation at reduced pressue. The product is heated at 150° C for 1 hour, cooled and the product is crystallized from ethanol to provide 3-[1,1-diphenyl-3-(2-azabicyclo[2.2.2]oct-2-yl)propyl]-5-methyl-1,2,4-oxadiazole, having the following structural formula

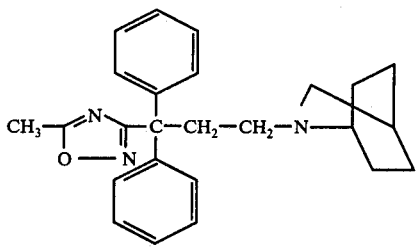

EXAMPLE 21

β-Thienyl-β-phenyl-β-imidazolyl propionic acid ethyl ester described in U.S. Pat. No 3,839,576 is with base and converted to the acid chloride with thionyl chloride and 2 parts of the acid chloride is reacted with 2 parts of 2-azabicyclo[2.2.2]octane in acetonitrile to provide the corresponding amide. 0.9 Parts of the amide is reduced with 0.37 parts of lithium aluminum hydride in 15 parts of tetrahydrofuran by methods set out in Example 1. The product obtained upon isolation is 2-[3-imidazolyl-3-phenyl-3-(2-thienyl)propyl]-2-azabicyclo-[2.2.2]octane. This compound has the following structural formula.

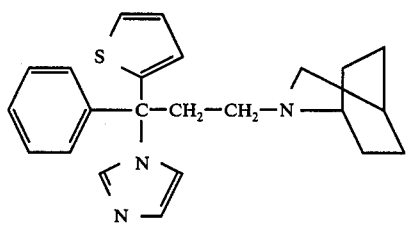

EXAMPLE 22

Reaction of 2.5 parts of diphenyl-3-pyridylmethane in 60 parts by volume of cyclohexane with an equivalent amount of butyl lithium at 10° C under nitrogen is followed by the addition of 2.1 parts of 4-(2-chloroethyl)-4-azatricyclo[4.3.1.1$^{3,8}$]undecane [preparable by mixing the hydrochloride thereof (U.S. Pat. No. 3,845,038) with excess aqueous sodium carbonate, extracting the mixture with toluene, and consecutively washing the extract with water, drying it over anhydrous sodium sulfate, filtering out the drying agent, and removing the solvent by vacuum distillation]. Quenching of the reaction with water and isolation by extraction with ether, washing, drying and evaporation of solvent provides 4-[3,3-(diphenyl)-3-(3-pyridyl)propyl[-4-azatricy- clo[4.3.1.1$^{3,8}$]undecane having the following structural formula

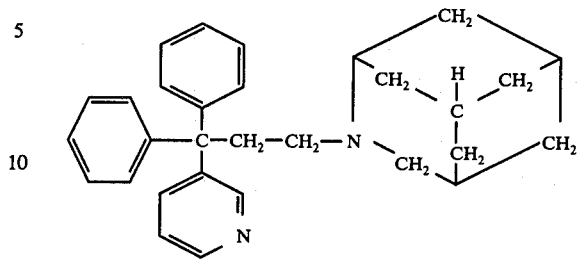

Originating this sequence of reaction with triphenylmethane and using equivalent quantities provides 4-(3,3,3-triphenylpropyl)-4-azatricyclo[4.3.1.1$^{3,8}$]undecane.

EXAMPLE 23

Following the procedures set out in Example 1, 9 parts of 3,3-diphenyl-3-(3-pyridyl)propionyl chloride and 27 parts of norpethidine are reacted in the presence of 4 parts of triethylamine in benzene solvent. The resulting amide is reduced with 5 parts of lithium aluminum hydride to provide 1-[3,3-diphenyl-3-(3-pyridyl)-propyl]-4-hydroxymethyl-4-phenylpiperidine having the following structure.

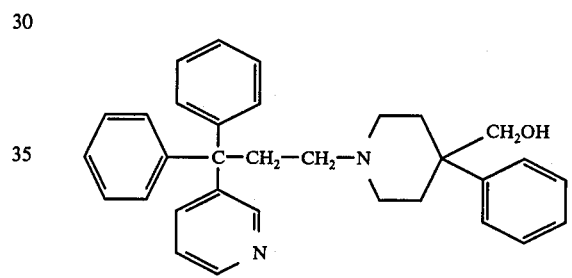

What is claimed is:
1. A compound of the formula

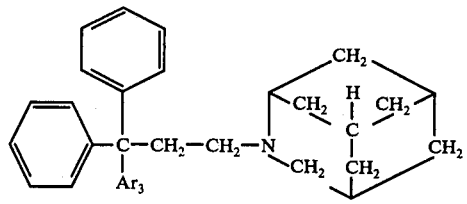

and the pharmaceutically acceptable acid addition salts thereof wherein Ar$_3$ is phenyl or pyridyl.

* * * * *